(12) United States Patent
Norred et al.

(10) Patent No.: US 11,291,473 B2
(45) Date of Patent: *Apr. 5, 2022

(54) UTERINE HEMORRHAGE CONTROLLING SYSTEM AND METHOD

(71) Applicant: ALYDIA HEALTH, INC., Menlo Park, CA (US)

(72) Inventors: Alexander James Norred, San Luis Obispo, CA (US); Davis Reed Carlin, Sammamish, WA (US); George Cochran Harper, Laguna Niguel, CA (US); David C. Lagrew, Jr., Irvine, CA (US); Amelia Michele Degenkolb, San Luis Obispo, CA (US)

(73) Assignee: Alydia Health, Inc., Menlo Park, CA (US)

( * ) Notice: Subject to any disclaimer, the term of this patent is extended or adjusted under 35 U.S.C. 154(b) by 405 days.

This patent is subject to a terminal disclaimer.

(21) Appl. No.: 16/035,543

(22) Filed: Jul. 13, 2018

(65) Prior Publication Data

US 2019/0083132 A1    Mar. 21, 2019

Related U.S. Application Data

(63) Continuation of application No. 13/827,579, filed on Mar. 14, 2013, now Pat. No. 10,064,651, which is a
(Continued)

(51) Int. Cl.
*A61B 17/42* (2006.01)
*A61B 17/12* (2006.01)
*A61B 17/30* (2006.01)

(52) U.S. Cl.
CPC .......... *A61B 17/42* (2013.01); *A61B 17/1204* (2013.01); *A61B 17/12136* (2013.01); *A61B 2017/306* (2013.01); *A61B 2217/005* (2013.01)

(58) Field of Classification Search
CPC .......................... A61F 13/00068; A61B 17/42
See application file for complete search history.

(56) References Cited

U.S. PATENT DOCUMENTS

| 1,928,992 A | 10/1933 | Clark et al. |
| 2,185,927 A | 1/1940 | Shelanski |

(Continued)

FOREIGN PATENT DOCUMENTS

| CA | 2952904 | 10/2015 |
| CN | 2097618 U | 3/1992 |

(Continued)

OTHER PUBLICATIONS

Hofmeyr, J.; Uterine suction devices: Review of literature and potential role; Effective care research unit, Univ. of the Witwatersrand/Fort Hare/Eastern Cape Dept. of Health; 22 pages; known of at least by Nov. 2018.

(Continued)

*Primary Examiner* — Adam Marcetich
*Assistant Examiner* — Meagan Ngo
(74) *Attorney, Agent, or Firm* — Shay Glenn LLP

(57) ABSTRACT

An embodiment of a uterine hemorrhage controlling system comprises a suction module including a suction end coupleable to a pump by a connecting tube, and a sealing module coupled to the suction module. The system may further comprise the pump and a filter coupled to the suction module. A uterine hemorrhage controlling method comprises: shielding a suction module that has been delivered into a uterus; sealing an entrance into the uterus while the suction module is situated within the uterus; applying a negative pressure within the uterus upon activation of a pump; and maintaining the negative pressure within the uterus to induce uterine contraction. The method may further comprise delivering the suction module into the uterus;

(Continued)

transmitting bodily fluids, out of the uterus through the suction module, and filtering the bodily fluids.

22 Claims, 10 Drawing Sheets

Related U.S. Application Data continuation-in-part of application No. 13/420,871, filed on Mar. 15, 2012, now Pat. No. 9,550,014.

(56) References Cited

U.S. PATENT DOCUMENTS

| | | | |
|---|---|---|---|
| 2,286,462 A | 6/1942 | Chaffin | |
| 2,400,251 A | 5/1946 | Nagel | |
| 2,483,851 A | 10/1949 | Smith | |
| 2,925,904 A | 2/1960 | Eichholz | |
| 2,981,255 A | 4/1961 | Heyns | |
| 3,062,215 A | 11/1962 | Heyns | |
| 3,517,665 A | 6/1970 | Sheldon | |
| 3,626,928 A | 12/1971 | Barringer et al. | |
| 3,670,732 A | 6/1972 | Robinson | |
| 3,774,613 A | 11/1973 | White et al. | |
| 3,828,781 A | 8/1974 | Rothman | |
| 3,835,843 A | 9/1974 | Karman | |
| 3,848,602 A | 11/1974 | Gutnick | |
| 3,923,051 A | 12/1975 | Soichet | |
| 3,929,133 A | 12/1975 | Ragab | |
| 4,013,079 A | 3/1977 | Lindemann et al. | |
| 4,111,209 A | 9/1978 | Wolvek et al. | |
| 4,141,360 A | 2/1979 | Lasswell | |
| 4,444,548 A | 4/1984 | Andersen | |
| 4,533,345 A | 8/1985 | Louw | |
| 4,552,557 A | 11/1985 | Rangaswamy | |
| 4,563,183 A | 1/1986 | Barrodale et al. | |
| 4,681,123 A | 7/1987 | Valtchev | |
| 4,767,404 A | 8/1988 | Renton | |
| 4,784,654 A | 11/1988 | Beecher | |
| 4,807,625 A | 2/1989 | Singleton | |
| 4,925,452 A | 5/1990 | Melinyshyn | |
| 4,955,875 A | 9/1990 | Knowles | |
| 4,981,477 A | 1/1991 | Schon et al. | |
| 5,030,202 A | 7/1991 | Harris | |
| 5,100,395 A | 3/1992 | Rosenberg | |
| 5,104,377 A | 4/1992 | Levine | |
| 5,160,325 A | 11/1992 | Nichols et al. | |
| 5,242,438 A | 9/1993 | Saadatmanesh et al. | |
| 5,254,084 A | 10/1993 | Geary | |
| 5,360,414 A | 11/1994 | Yarger | |
| 5,431,173 A | 7/1995 | Chin et al. | |
| 5,451,208 A | 9/1995 | Goldrath | |
| 5,464,409 A | 11/1995 | Mohajer | |
| 5,472,435 A * | 12/1995 | Sutton | A61M 25/005 604/540 |
| 5,569,284 A | 10/1996 | Young et al. | |
| 5,603,685 A | 2/1997 | Tutrone, Jr. | |
| 5,769,880 A | 6/1998 | Truckai et al. | |
| 5,800,414 A | 9/1998 | Cazal | |
| 5,807,282 A | 9/1998 | Fowler | |
| 5,928,249 A | 7/1999 | Saadat et al. | |
| 5,941,873 A | 8/1999 | Korenfeld | |
| 6,350,463 B1 | 2/2002 | Herman et al. | |
| 6,443,947 B1 | 9/2002 | Marko et al. | |
| 6,506,149 B2 | 1/2003 | Peng et al. | |
| 6,508,815 B1 | 1/2003 | Strul et al. | |
| 6,641,575 B1 * | 11/2003 | Lonky | A61B 17/00234 600/210 |
| 6,676,680 B1 | 1/2004 | Packer | |
| 6,736,822 B2 | 5/2004 | McClellan et al. | |
| 7,247,141 B2 | 7/2007 | Makin et al. | |
| 7,325,546 B2 | 2/2008 | Burbank et al. | |
| 7,512,445 B2 | 3/2009 | Truckai et al. | |
| 7,708,716 B2 | 5/2010 | Shah | |
| 8,197,470 B2 | 6/2012 | Sharkey et al. | |
| 8,221,401 B2 | 7/2012 | Sharkey et al. | |
| 8,287,552 B2 | 10/2012 | Grillo | |
| 9,125,686 B2 | 9/2015 | Norred | |
| 9,301,770 B2 | 4/2016 | Gruber | |
| 9,550,014 B2 | 1/2017 | Norred et al. | |
| 9,763,731 B2 | 9/2017 | Dubois et al. | |
| 9,919,083 B2 | 3/2018 | Blin | |
| 10,064,651 B2 | 9/2018 | Norred et al. | |
| 2002/0010457 A1 | 1/2002 | Duchon et al. | |
| 2003/0064746 A1 | 4/2003 | Rader et al. | |
| 2003/0191452 A1 | 10/2003 | Meglin et al. | |
| 2004/0006331 A1 | 1/2004 | Shchervinsky | |
| 2004/0122352 A1 | 6/2004 | John | |
| 2004/0220550 A1 | 11/2004 | Schryver | |
| 2005/0261663 A1 | 11/2005 | Patterson et al. | |
| 2006/0015089 A1 | 1/2006 | Meglin et al. | |
| 2007/0032814 A1 | 2/2007 | Hibler | |
| 2007/0149998 A1 | 6/2007 | Wicks et al. | |
| 2008/0045924 A1 | 2/2008 | Cox et al. | |
| 2008/0051708 A1 | 2/2008 | Kumar et al. | |
| 2008/0188863 A1 | 8/2008 | Cho | |
| 2008/0319472 A1 | 12/2008 | Shelley | |
| 2009/0048685 A1 | 2/2009 | Frigstad et al. | |
| 2009/0093795 A1 | 4/2009 | Koeper | |
| 2010/0069886 A1 | 3/2010 | Wilkes | |
| 2010/0191279 A1 | 7/2010 | Kassab et al. | |
| 2010/0198214 A1 | 8/2010 | Layton, Jr. et al. | |
| 2010/0228239 A1 | 9/2010 | Freed | |
| 2010/0274260 A1 | 10/2010 | D'Arpiany et al. | |
| 2011/0087337 A1 | 4/2011 | Forsell | |
| 2011/0098524 A1 | 4/2011 | Barcelo Rojas | |
| 2011/0208178 A1 | 8/2011 | Truckai | |
| 2012/0041419 A1 | 2/2012 | Blanchard et al. | |
| 2012/0071841 A1 | 3/2012 | Bengtson | |
| 2012/0172889 A1 * | 7/2012 | Chin | A61B 17/32002 606/119 |
| 2013/0245637 A1 | 9/2013 | Norred et al. | |
| 2013/0266165 A1 | 10/2013 | Neumeyer | |
| 2013/0296816 A1 | 11/2013 | Greener | |
| 2014/0079241 A1 | 3/2014 | Chan et al. | |
| 2014/0163532 A1 | 6/2014 | Cornet et al. | |
| 2014/0200591 A1 | 7/2014 | Sullivan et al. | |
| 2014/0228801 A1 | 8/2014 | Keeling | |
| 2014/0228877 A1 | 8/2014 | Kassab et al. | |
| 2015/0080861 A1 | 3/2015 | Ozer | |
| 2015/0165151 A1 | 6/2015 | Payton et al. | |
| 2017/0035949 A1 | 2/2017 | Loske | |
| 2017/0281231 A1 | 10/2017 | Langell et al. | |
| 2018/0055523 A1 | 3/2018 | Bair et al. | |
| 2019/0216504 A1 | 7/2019 | Norred et al. | |
| 2020/0352602 A1 | 11/2020 | Norred et al. | |

FOREIGN PATENT DOCUMENTS

| | | |
|---|---|---|
| CN | 2116469 U | 9/1992 |
| CN | 2149183 Y | 12/1993 |
| CN | 2254720 Y | 5/1997 |
| CN | 2415733 Y | 1/2001 |
| CN | 2464264 Y | 12/2001 |
| CN | 2467062 Y | 12/2001 |
| CN | 2559321 Y | 7/2003 |
| CN | 2565407 Y | 8/2003 |
| CN | 2633227 Y | 8/2004 |
| CN | 2662850 Y | 12/2004 |
| CN | 2933317 Y | 8/2007 |
| CN | 201185945 Y | 1/2009 |
| CN | 101366650 A | 2/2009 |
| CN | 201337472 Y | 11/2009 |
| CN | 201356633 Y | 12/2009 |
| CN | 201361088 Y | 12/2009 |
| CN | 202044560 U | 11/2011 |
| CN | 202146327 U | 2/2012 |
| CN | 202288422 U | 7/2012 |
| CN | 203122506 U | 8/2013 |
| CN | 107427659 A | 12/2017 |
| GB | 839965 A | 6/1960 |
| GB | 1469584 A | 4/1977 |
| IN | 200300065 I3 | 1/2005 |
| IN | 5953/CHE/2014 | 2/2015 |

(56) References Cited

FOREIGN PATENT DOCUMENTS

| IN | 4745CHE2015 | | 8/2016 |
|---|---|---|---|
| JP | 05305145 | | 11/1993 |
| JP | 2001513357 | A | 9/2001 |
| JP | 2007523716 | A | 8/2007 |
| KR | 20010002164 | A | 1/2001 |
| RU | 2113246 | C1 | 6/1998 |
| RU | 98112 | U1 | 10/2010 |
| RU | 102509 | U1 | 3/2011 |
| RU | 2429792 | C1 | 9/2011 |
| RU | 2440038 | C2 | 1/2012 |
| SU | 1426560 | A1 | 9/1988 |
| SU | 1431746 | A1 | 10/1988 |
| WO | WO2001/080788 | A2 | 11/2001 |
| WO | WO 2011/097350 | | 8/2011 |
| WO | WO2012/137894 | A1 | 10/2012 |
| WO | WO2021/016564 | A1 | 1/2021 |

OTHER PUBLICATIONS

Video of B2B Competition 2016, Bench 2 Bedside Student Program, Specifically 0:42 in the Video, [Copy Not Enclosed], Can be Viewed at <URL:http://uofuhealth.utah.edu/center-for-medical-innovation/backup_folder/index-old.php.

Video of Panickers PPH Suction Device, Vasudeva Panicker, Published Apr. 9, 2015, [Copy Not Enclosed], Can be Viewed at <URL: https://www.youtube.com/watch?v=KDa_tLp3qVM.

Video of Dr. Panicker's PPH Suction Device—INSTASTOP, Vasudeva Panicker, Published Jan. 26, 2017, [Copy Not Enclosed], Can be Viewed at <URL: https://www.youtube.com/watch?v=a-QIpkeT3Gg>.

Video of Panicker's PPH Suction Device, Vasudeva Panicker, Published Oct. 25, 2016, [Copy Not Enclosed], Can be Viewed at <URL: https://www.youtube.com/watch?v=uQYoWEbWJOg.

Video of Webinar On Managing Atomic PPH Using Vacuum Retraction Cannula, Docplexus, Published Oct. 25, 2016. [Copy Not Enclosed], Can be Viewed at <URL: https://www.youtube.com/watch?v=FSpn8JLSQtA.

United States Office Action, U.S. Appl. No. 13/827,579, dated Dec. 28, 2017, 16 pages.

United States Office Action, U.S. Appl. No. 13/827,579, dated Jul. 1, 2016, 17 pages.

United States Office Action, U.S. Appl. No. 13/827,579, dated Dec. 17, 2015, 12 pages.

Balloon Uterine Stent, Cook Medical, Cook, 2017, 3 pages, [Online] [Retrieved on Dec. 21, 2017] Retrieved from the Internet <URL:https://www.cookmedical.com/products/wh_bus_webds/>.

Ebb—Clinical Innovations—forMOM. forBABY. forLIFE, Clinical Innovations, LLC, 2016, 6 pages, [Online] [Retrieved on Dec. 21, 2017] Retrieved from the Internet <URL:http://clinicalinnovations.com/portfolio-items/ebb/>.

Ebb, Complete Tamponade System, Clinical Innovations, LLC, undated, 2 pages, [Online] [Retrieved on Dec. 21, 2017] Retrieved from the Internet <URL: http://clinicalinnovations.com/wp-content/uploads/2017/04/056-0086-Rev.-B.pdf>.

Manage Postpartum Hemorrhage, Bakri, Postpartum Balloon With Rapid Instillation Components, Cook, Mar. 2017, 4 pages, [Online] [Retrieved on Dec. 21, 2017] Retrieved from the Internet <URL: https://www.cookmedical.com/data/resources/RH-D28438-EN-F_M3_1489434681697.pdf>.

Panicker, T.N.V., "Panicker's Vacuum Suction Haemostatic Device for Treating Post-Partum Haemorrhage," The Journal of Obstetrics and Gynocology of India, Mar.-Apr. 2017, pp. 150-151, vol. 67, No. 2, [Online] [Retrieved on Mar. 26, 2018] Retrieved from the Internet <URL:http://www.jogi.co.in/march_april_17/pdf/14_iat.pdf>.

Goates, T. et al.; Poster: UVAC Uterine Vacuum Assisted Contraction, University of Utah Health Science, Center for Medical Innovation, Bench to Bedside, Apr. 2016.

Postpartum Hemorrhage PPH Bakri Style Balloon BT—Cath Balloon Tamponade Catheter, Utah Medical Products Inc., 1999-2017, 3 pages, [Online] Retrieved from the Internet <URL:http://www.utahmed.com/bt-cath.html>.

Ram, S. et al., "Vacuum Retraction of Uterus for the Management of Atonic Postpartum Hemorrhage," IOSR Journal of Dental and Medical Sciences (IOSR-JDMS), Nov. 2014, pp. 15-19, vol. 13, Issue 11, Ver. III. May be Retrieved at <URL: https://www.researchgate.net/publication/284005732_Vacuum_retraction_of_ute rus_for_the_management_of_atonic_postpartum_hemorrhage>.

Uchida et al.; U.S. Appl. No. 17/311,724 entitled "Postpartum uterine hemorrhage device," filed Jun. 8, 2021.

* cited by examiner

149'''       148'''

UTERINE HEMORRHAGE CONTROLLING SYSTEM AND METHOD

CROSS-REFERENCE TO RELATED APPLICATIONS

This application is a continuation of U.S. patent application Ser. No. 13/827,579, filed Mar. 14, 2013, which is a continuation-in-part of U.S. patent application Ser. No. 13/420,871, filed Mar. 15, 2012, now U.S. Pat. No. 9,550,014, each of which are incorporated herein by reference in their entireties for all purposes.

TECHNICAL FIELD

This invention relates generally to the medical device field, and more specifically to an improved uterine hemorrhage controlling system and method.

BACKGROUND

Postpartum hemorrhage, defined as excessive blood loss after birth, is the leading cause of maternal death in the world, claiming the lives of over 125,000 mothers every year. Inability to control postpartum bleeding can require a woman to receive multiple blood transfusions, and in severe cases, a full hysterectomy. Accordingly, it is desirable to control such postpartum bleeding, if possible, at its onset. The cause of postpartum hemorrhage, in approximately 80% of cases, is uterine atony, which is the inability of the woman's uterus to contract after delivering the child. Risk factors for uterine atony include prolonged stage of labor, preeclamsia, and multiparity.

Postpartum hemorrhage has been traditionally treated using oxytoxic agents, hormonal agents that induce muscle contraction. Unfortunately, studies have increasingly shown that oxytoxic agents do not significantly reduce either the incidence of postpartum hemorrhage or the amount of blood lost. Some studies have even indicated that oxytoxic agents are being overused to the point that this treatment increases the risk of uterine atony. Current medical devices and surgical procedures have also proven inadequate in reducing postpartum hemorrhage or the amount of blood lost, and/or are extremely invasive.

It has recently been discovered by the inventors that providing negative pressure within the uterus, in combination with sealing an opening to the uterus or vagina at the distal end, can rapidly induce uterine contraction to counteract uterine atony, thus reducing or entirely stopping uterine hemorrhaging. Providing negative pressure may furthermore be performed in a non-invasive (i.e., non-surgical) manner, effectively removing an inadequacy of other hemorrhage-controlling options. With the knowledge of this discovery, the inventors have created an improved uterine hemorrhage controlling system and method.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. System

Figure 1:
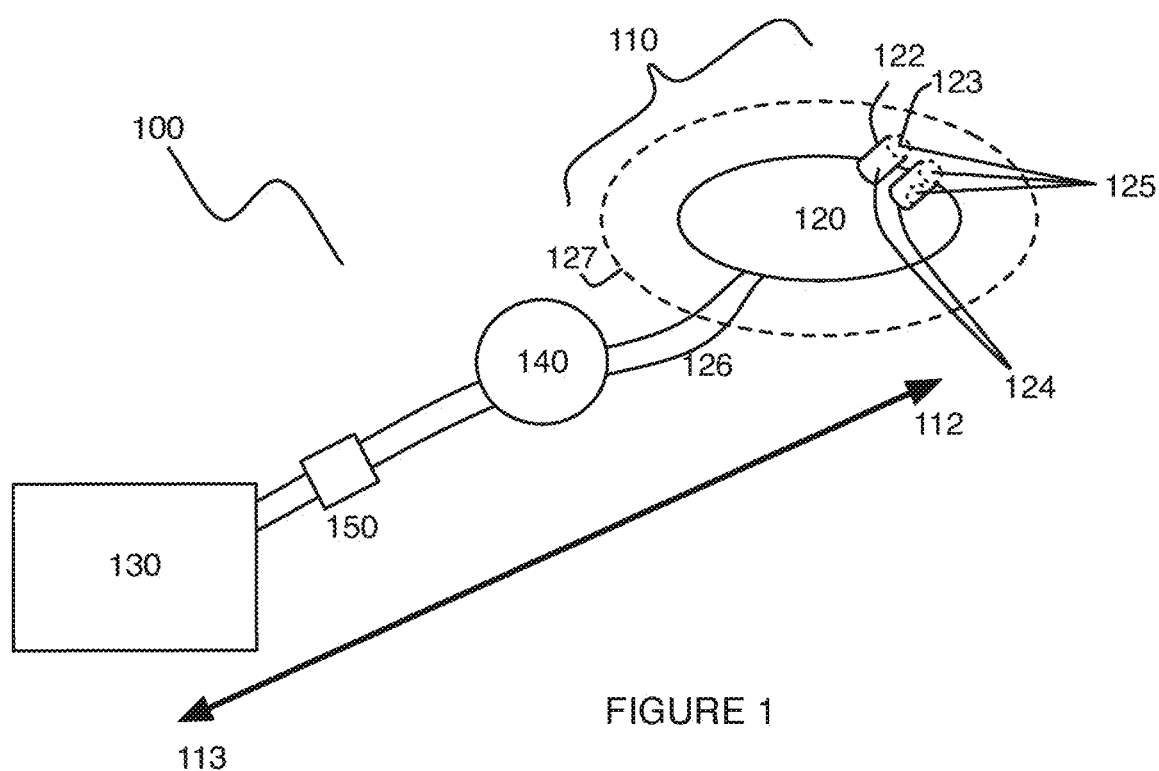
FIG. 1 depicts an embodiment of a uterine hemorrhage controlling system.

As shown in FIG. 1, an embodiment of a uterine hemorrhage controlling system 100 comprises a suction module 110 including a suction end 120 coupleable to a pump 130 by a connecting tube 126, and a sealing module 140 coupled to the suction module 110. The system 100 may further comprise the pump 130 and a filter 150 coupled to the suction module 110. At least a portion of the system 100 is preferably delivered transvaginally, and facilitates contraction of the uterus to counteract uterine atony. Thus, the system 100 functions to reduce or entirely stop uterine hemorrhaging, in order to substantially reduce total blood lost from the uterus after childbirth. The system 100 may further function to reduce other issues associated with childbirth, including a need for a blood transfusion or a hysterectomy.

1.1 System—Suction Module

The suction module 110 comprises a suction end 120 coupleable to a pump 130 by a connecting tube 126, and functions to provide negative pressure within the uterus to facilitate uterine contraction. Preferably, negative pressure provided by the suction module 110 results in a uniform mechanical stimulus to the uterine wall, in order to facilitate substantially even contractile movement of tissue; however, the suction module 110 may alternatively be configured to provide a non-uniform mechanical stimulus to the uterine wall, or to decrease intra-uterine pressure and/or volume by any suitable method (e.g., mechanically, chemically, creation of a vacuum, reduction in intrauterine temperature). The suction module 110 preferably comprises a distal end 112 and a proximal end 113, as shown in FIG. 1, wherein the distal end 112 comprises the suction end 120 and is configured to enter the uterus, and the proximal end 113 comprises the pump 130 and is configured to remain external to the uterus. However, both the distal end 112 and the proximal end 113 may be configured to enter the uterus. Preferably, the distal end 112 and the proximal end 113 are coupled by the connecting tube 126 (e.g., by a conduit, tubing, chamber), and may be further configured to be reversibly coupled in variations wherein at least one of the distal end 112 and the proximal end 113 is configured to be disposable. In some variations, the suction module 110 may further comprise a pressure sensor and/or a controller, which functions to facilitate measurement of a pressure provided by the pump 130 and/or a pressure within the uterus, and also to controllably adjust a negative pressure provided within the uterus.

The suction end 120 is configured to be transvaginally delivered, and functions to transmit a negative pressure provided by the pump 130 to the interior of the uterus, while preventing tissue or any other substance within the uterus from obstructing the suction end 120. The suction end 120 is preferably flexible, and may be further configured to be deformed into one or more configurations. Flexibility in the suction end 120 may further function to facilitate conformation of the suction end 120 to the intra-uterine anatomy of the patient. Variations of a flexible suction end 120 may be configured to be reversibly or irreversibly deformable. Alternatively, the suction end 120 may be rigid and substantially non-deformable, or may be configured to be rigid in one environment, and transition to a flexible state in another environment. Preferably, the suction end 120 is composed or partially composed of a medical-grade material (e.g., polyethylene, polypropylene, stainless steel, cobalt chrome, ceramic), such that the suction end 120 does not induce an adverse reaction after being inserted into a uterus of the patient. The suction end 120 may further be configured to prevent or counteract an inflammatory or biorejection response by processing the suction end material with anti-inflammatory and/or anti-biorejection agents (e.g., steroidal or non-steroidal anti-inflammatory agents). However, the suction end 120 may alternatively be composed of any suitable material that does not prevent the suction end 120 from transmitting a negative pressure to the interior of the uterus.

Preferably, at least a portion of the suction end 120 is configured to be disposable, such that the suction module 110 is modular and comprises components that may be removably attached together. In variations of a modular suction module 110, attachment locations between various components are preferably configured to provide hermetic seals, in order to prevent fluid and/or air leakage along the suction module 110. At least a portion of the suction end 120 may alternatively be configured to be reusable, and may or may not comprise hermetic seals at locations of coupling. In variations wherein a portion of the suction end 120 is configured to be reusable, the suction end 120 preferably comprises a material that may be sterilized without compromising the function of the suction end 120. The material may be configured to be sterilized by dry heat sterilization, moist heat sterilization, ethylene oxide sterilization, radiation (e.g., ultraviolet, gamma, electron beam), liquid chemical sterilization, or any other suitable sterilization method. In a specific example, the material is configured to be sterilized according to the U.S. Food and Drug Administration 510(k) Sterility Review Guidance K90-1.

The suction end 120 of the preferred embodiments includes a suction tube 122 and a shield 127 coupled to a distal portion of the suction tube 122 configured to enter the uterus. The suction end 120 may, however, omit the shield 127 in other embodiments. The suction tube 122 comprises an opening 123 fluidically coupled to a lumen of the connecting tube 126, which functions to allow a negative pressure to be transmitted from the pump 130, through the connecting tube 126, to the uterus. Preferably, the suction tube 122 is flexible, as described above; however, the suction tube 122 may alternatively be non-flexible or undergo a transition from a flexible state to a rigid state in different environments. Additionally, the suction tube 122 may be one of a set of suction tubes 124 coupled to the pump 130, such that the suction end 120 has an inherent redundancy of suction tubes configured to allow a negative pressure to be transmitted into the uterus. Furthermore, the suction tube(s) may comprise a set of openings 125, the suction tube(s) may be configured to have a curved portion, and/or the suction tube(s) may be configured to have a non-curved portion. Additionally, the suction tube(s) 122 may have any suitable length, diameter, or cross-sectional shape (e.g., uniform, non-uniform) configured to facilitate provision of a negative pressure within the uterus.

In a first variation, the suction end 120 comprises a single suction tube 122 with a single opening 123. In an example of the first variation, a lumen of the single suction tube 122 terminates in the single opening 123 at a distal end of the suction tube 122, and in another example of the first variation, the single opening 123 is located at any point along the length of the suction tube 122. In a second variation, the suction end 120 comprises a single suction tube 122 with a set of openings 125. In a third variation, the suction end 120 comprises a set of suction tubes 124 with a set of openings 125. In other variations, the suction end 120 may have any suitable combination of the above variations, or any suitable configuration to facilitate provision of a negative pressure within the uterus.

The shield 127 functions to provide a barrier, in order to prevent obstruction of the opening(s) of the suction tube 122 or set of suction tubes 124 by uterine tissue or any other substance within the uterus. The shield 127 is preferably coupled to a distal portion of the suction tube 122 or set of suction tubes 124 configured to enter the uterus, but may be coupled to any suitable portion of the suction module 110 or suction tube 122 to prevent obstruction. The shield 127 is preferably composed of a medical-grade material, such as a medical-grade metal or polymer, but may be composed of any suitable material to prevent obstruction of the opening(s). Additionally, the shield 127 may be rigid or flexible.

Figures 2A, 2B:
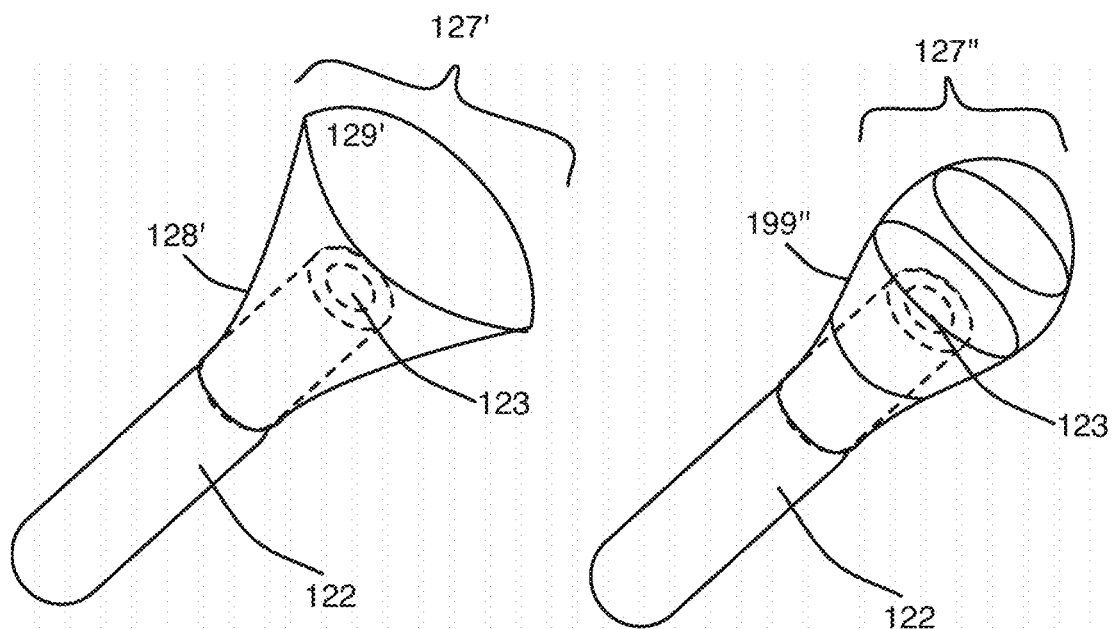
FIGS. 2A-2C depict variations of a suction tube and shield of an embodiment of a uterine hemorrhage controlling system.
Figures 2C, 3A:
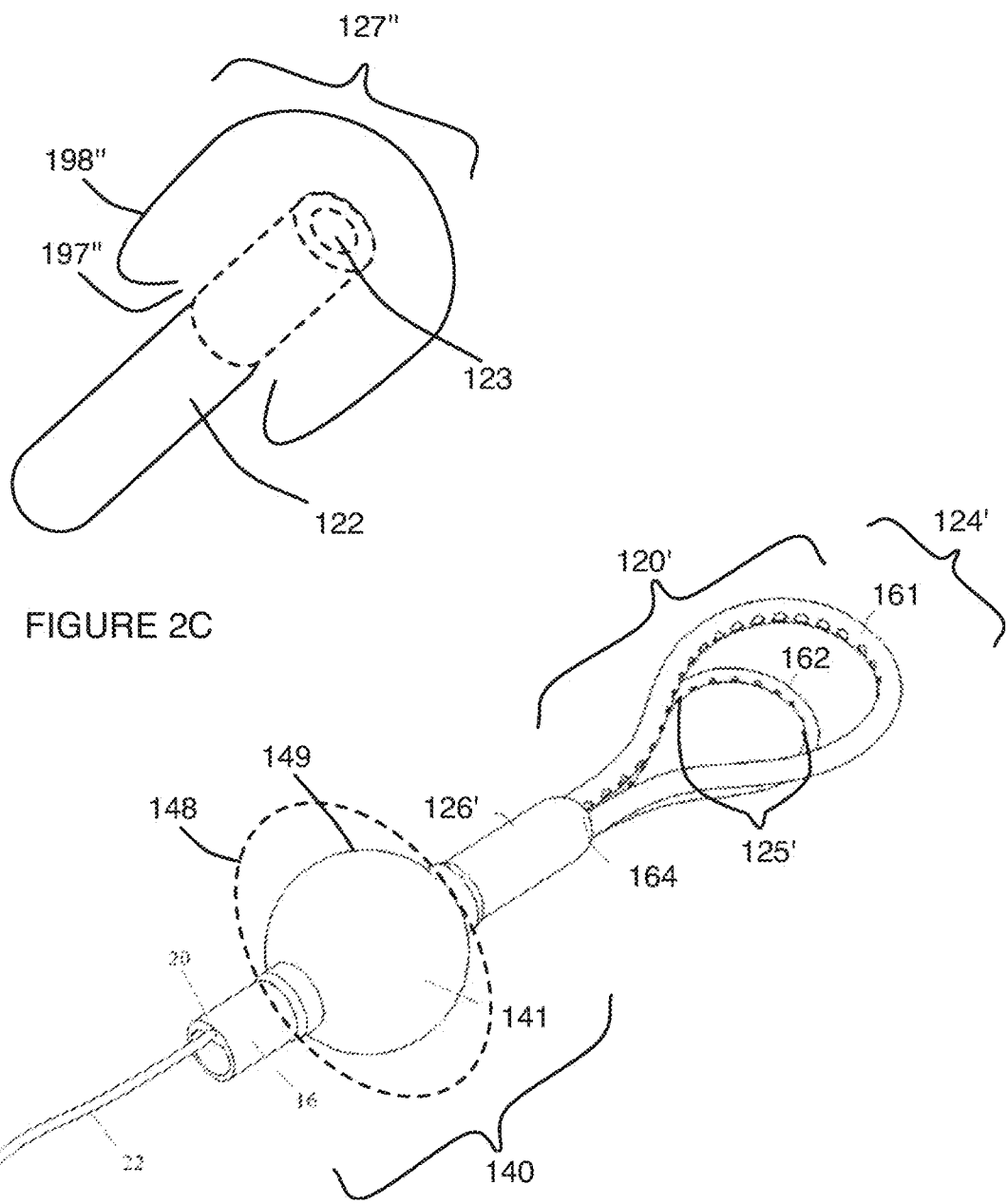
FIG. 3A depicts a specific example of a uterine hemorrhage controlling system.

In a first variation, the shield 127' is configured to couple to a portion of a suction tube 122 and diverge outward from the suction tube 122 at least at a location of an opening 123 to form a perimeter, such that uterine tissue or other tissue is prevented from impinging upon the opening 123. In an example of the first variation, the shield 127' comprises a conical or pyramidal surface 128' that flanks a suction tube 122 and that has an open mouth 129' that extends beyond a distal end of the suction tube 122, as shown in FIG. 2A. In a second variation, the shield 127" may partially encapsulate an opening 123 (e.g., by a cage or a frame) to prevent obstruction of the opening 123. In an example of the second variation, as shown in FIG. 2B, the shield 127" may form a bulbous cage 199" about an opening 123. The dimensions of the bulbous cage are preferably smaller than the atonic uterus, such that sufficient contraction may be enabled, and smaller than the vagina opening, such that correct position may be reached. In another example of the second variation, as shown in FIG. 2C, the shield 127" may form a capsule 198" about an opening, wherein the body of the capsule 198" prevents obstruction of an opening 123 of the suction tube 122, and wherein the capsule has an hole 197" configured to allow the suction tube 122 to facilitate creating of a negative pressure within the uterus. The shield 127 may, however, comprise any suitable geometry and/or configuration to prevent obstruction of the opening(s) of the suction tube 122 or set of suction tubes 124.

In alternative variations, the suction tube 122 or the set of suction tubes 124 may be configured to also function as a shield 127 (or to be physically coextensive with the shield).

In these alternative variations, the suction tube 122 or the set of suction tubes 124 thus functions to simultaneously allow a negative pressure to be applied within the uterus, while preventing obstruction of suction tube opening(s). This dual-functionality may be enabled by strategic placement of the opening(s) 123, 125 of the suction tube(s) 122, 124, and/or by geometrically configuring the suction tube(s) to prevent obstruction of an opening or openings.

Figure 3B:
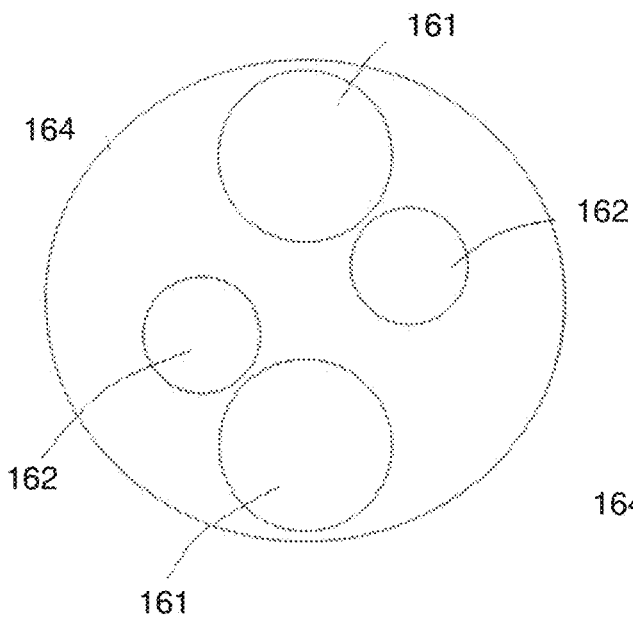
FIGS. 3B and 3C depict cross-sectional views of suction tube connecting joints.
Figure 3C:
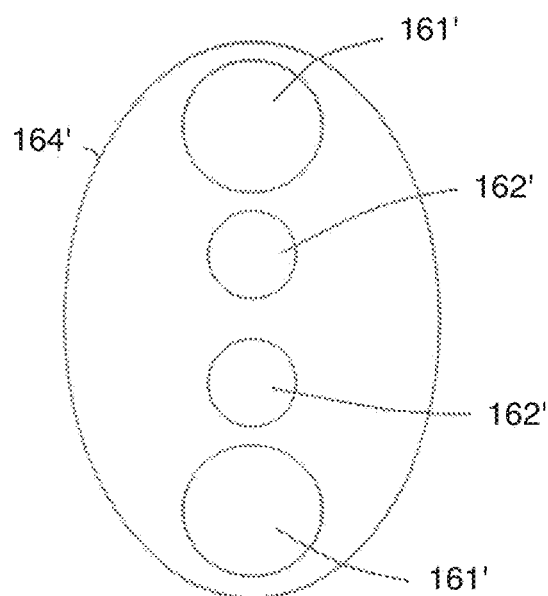

In a first variation of an embodiment wherein the suction tube(s) function as a shield, the suction end 120' may comprise a set of curved suction tubes 124' connected to a connecting tube 126 coupleable to the pump 130, as shown in FIG. 3A. In an example of the first variation, the set of curved suction tubes 124' may comprise a first suction tube 161 and a second suction tube 162 that are arranged in loops that extend different distances. As shown in the cross sections of FIGS. 3B and 3C, the first suction tube 161 and the second suction tube 162 may be coupled to the connecting tube 126 by a joint 164. In the example, the first suction tube 161 may have a longer length and extend in a wider loop from the distal end 112 of the suction module, and the second suction tube 162 may have a shorter length and be configured in a loop that is within the loop created by the first suction tube 161. The first suction tube 161 and the second suction tube 162 in the example may have identical or non-identical cross sections (e.g., dimensions, geometry, lumen configurations), a maximum cross sectional dimension between 25 mm and 125 mm, and substantially smooth surfaces to prevent abrasion within the vagina/uterus. The set of curved suction tubes 124' in the first example is composed of a medical-grade material that is flexible enough to conform to intra-uterine anatomy, but rigid enough to maintain fixed angles at the point of connection between the set of curved suction tubes 124' and the connecting tube 126. The medical-grade material in the example has a Shore A hardness value between 50 and 90. In the example of the first variation, the set of curved suction tubes 124' comprises up to eight suction tubes 122'.

Figure 3D:
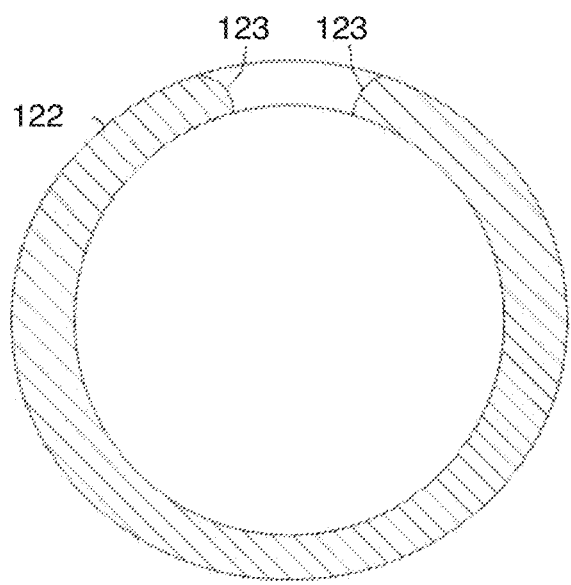
FIG. 3D shows an example of a suction tube cross section and opening.

In the example of the first variation, each suction tube 122' in the set of curved suction tubes 124' comprises a lumen that is coupled, by the connecting tube 126', to the pump 130, and also connected to a set of openings 125'. A negative pressure provided by the pump 130 therefore facilitates uterine contraction and allows intra-uterine fluids to flow through a set of openings 125' into the lumen of a suction tube 122'. The set of openings 125' in the example are oriented to open along a medial surface of a suction tube 161,162 to prevent uterine tissue or other tissue from obstructing the set of openings 125'. The set of openings 125' in the example comprises openings 123' that are between 1 and 6 mm in diameter, and are also substantially smooth and rounded, as shown in the cross-section of FIG. 3D, to prevent damage to the uterus or other tissues.

Figure 4A:
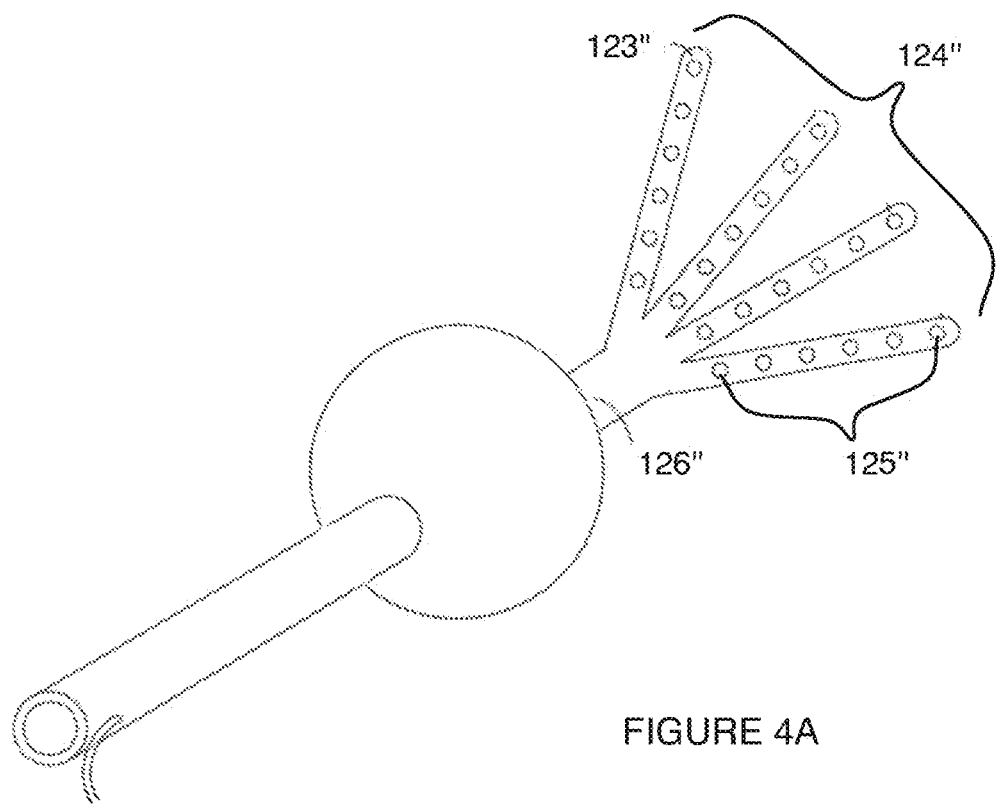
FIGS. 4A and 4B depict examples of suction tubes that also function as shields.

In a second variation of an embodiment wherein the suction tube(s) function as a shield 127, the set of suction tubes 124" branch from the connecting tube 126", and at least one of the set of suction tubes 124" comprises a set of openings 125" along a medial surface of a suction tube of the set of suction tubes 124". The branched configuration functions to prevent tissue from obstructing the medially oriented openings. In an example of the second variation, as shown in FIG. 4A, the set of suction tubes 124" comprises openings 123" that are between 1 and 6 mm in diameter, and up to 16 suction tubes with smooth and/or rounded edges to prevent damage to the uterus or other tissues.

Figure 4B:
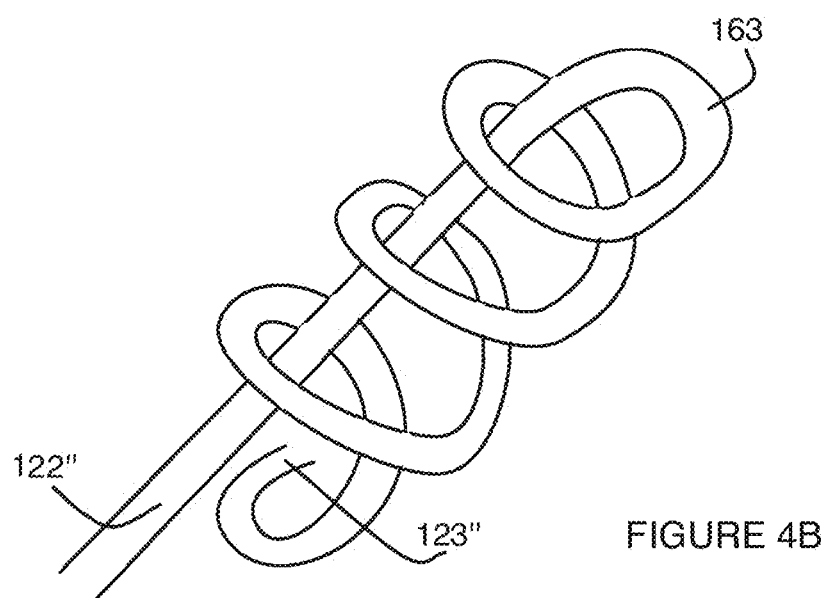

In a third variation of an embodiment wherein the suction tube(s) function as a shield 127, a suction tube 122'" or a set of suction tubes 124'" may comprise a turnabout portion 163 configured to prevent an opening from being obstructed. In an example of the third variation, a turnabout portion 163 of a suction tube 122'" may be configured to wrap around itself along a portion of the length of the suction tube 122", as shown in FIG. 4B. In another example, a set of suction tubes 124" may comprise a suction tube 122'" with a turnabout portion 163 configured to partially wrap around a length of the set of suction tubes 124'". Alternatively, the turnabout portion 163 may not be configured to partially wrap about a suction tube 122'", but may still provide a shield 127 by providing a barrier to prevent obstruction of an opening.

Figure 4C:
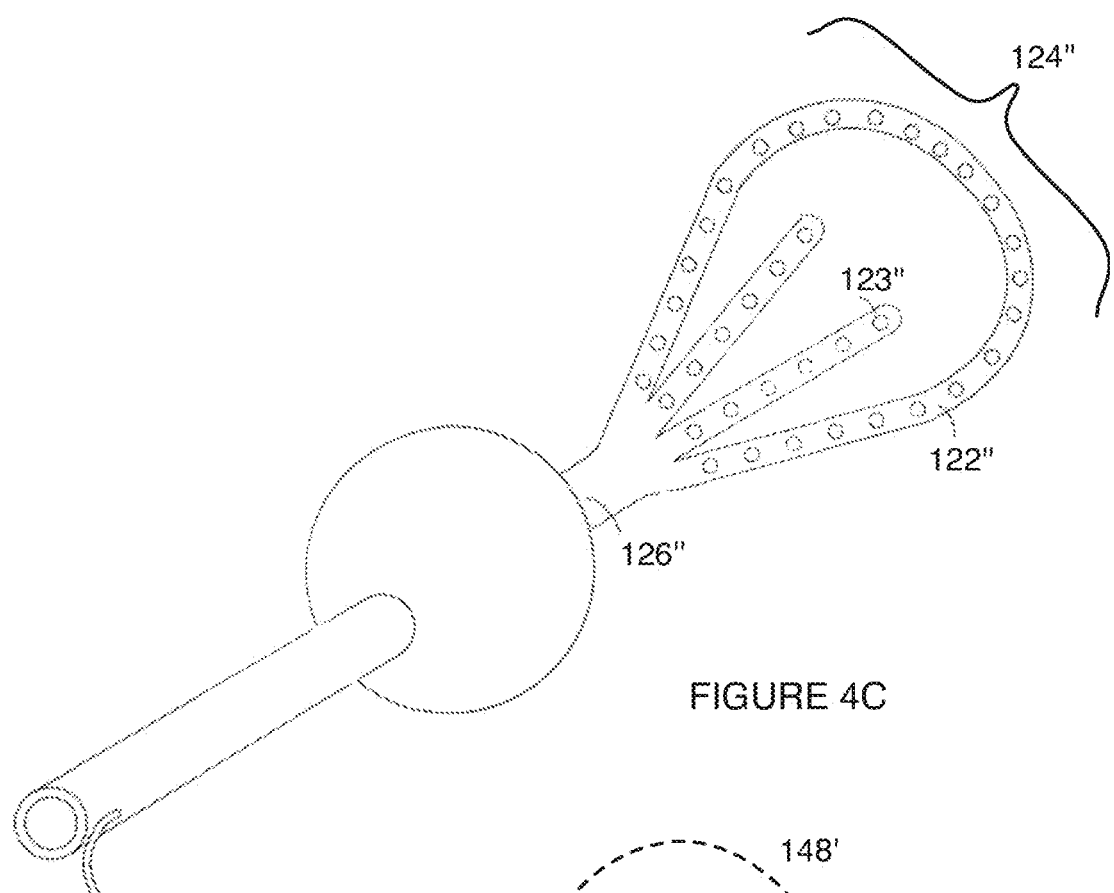
FIG. 4C depicts an example of a system that combines variations of elements.

Other variations of the suction tube(s) 122, 124, shield 127, and/or dual-functioning suction tube(s) may comprise any suitable combination of the above variations, an example of which is shown in FIG. 4C.

1.2 System—Sealing Module

The sealing module 140, which is preferably proximal to the suction end 120 and comprises a deformable seal 142, functions to provide a seal such that negative pressure may be maintained within the uterus to facilitate contraction of the uterus. The sealing module 140 may be configured to provide a seal at any point from the vulva, the cervix, or any point within the uterus, but preferably provides a seal at a point along the vagina distal to the uterus. The sealing module 140 may also be configured to be deformable, such that the sealing module 140 has more than one configuration; however, the sealing module 140 may be configured to be substantially non-deformable, such that the sealing module 140 only has a single configuration. Preferably, a complete seal (e.g., airtight/hermetic) is provided by the sealing module 140, such that a negative pressure is maintained within the uterus even after the pump 130 is deactivated; however, a non-complete seal may be provided by the sealing module 140, such that an adequate negative pressure is transmitted to the uterus while the pump 130 is activated, but the negative pressure is not maintained after the pump 130 is deactivated. Furthermore, at least a portion of the sealing module 140 may be configured to be disposable, and at least a portion of the sealing module 140 may be configured to be reusable.

In a first variation, the sealing module 140 is configured to provide a seal within the vaginal canal and/or at the cervix. In the first variation, the sealing module 140 may comprise a seal 141 that is configured to deform, reversibly or irreversibly, into at least two configurations. A first configuration 148 preferably activates the seal, and a second configuration 149 preferably deactivates the seal. Producing the first configuration may involve an expansion (e.g., radial, axial, uniform, non-uniform, isotropic, non-isotropic) of the seal 141, and producing the second configuration 149 may involve a contraction (e.g., radial, axial, uniform, non-uniform, isotropic, non-isotropic) of the seal 141. Producing the first configuration 148 may alternatively involve releasing a constrained seal 141, and producing the second configuration may involve constraining a released seal 141. However, the seal 141 in the first variation may be a non-deformable seal that has a single configuration.

Figure 5A:
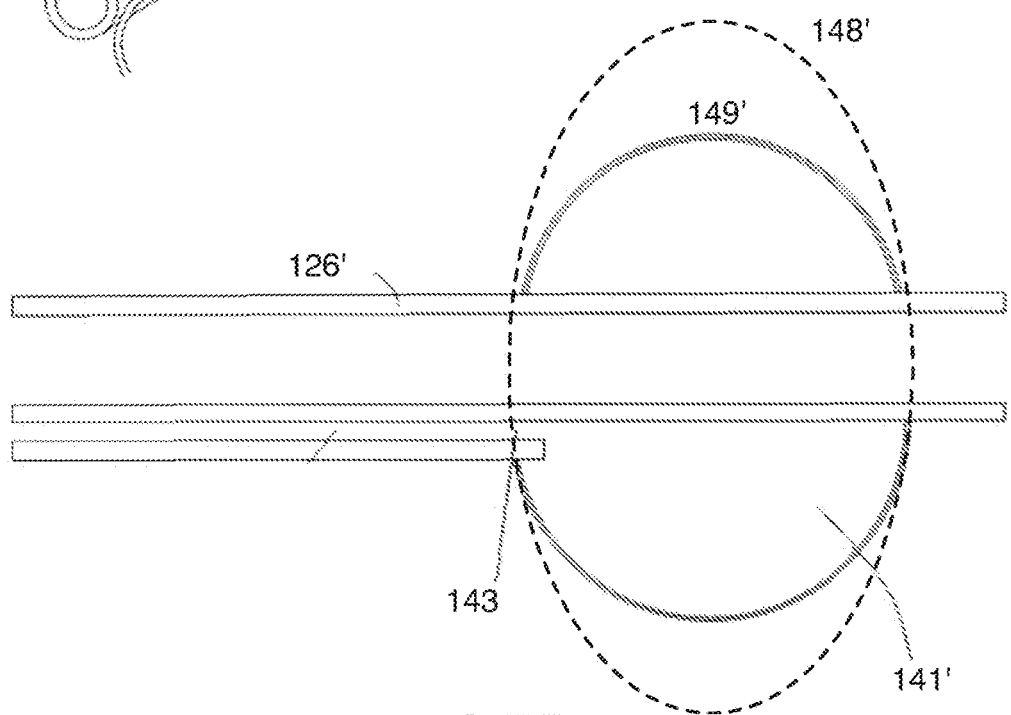
FIGS. 5A-5B depict examples of an inflatable sealing module element.

In a first specific example of the first variation, as shown in FIGS. 3A and 5A, the seal 141' is an inflatable balloon configured to deform into an expanded configuration 148' and a contracted configuration 149'. Upon delivering the suction end 120 transvaginally, the seal 141' in the first specific example is configured to be situated, in the contracted configuration 149', within the vaginal canal. The seal 141' may then be expanded to produce an expanded configuration 148' that seals the vagina in order to facilitate maintenance of a negative pressure within the uterus. In the first specific example, the seal may be expanded isotropically by delivering a fluid (e.g., saline or water) or a gas (e.g., air, nitrogen) to the interior of the inflatable balloon from a source external to the seal through an opening into the inflatable balloon. The expanded configuration 148' of the seal in the first specific example substantially fills the entire cross section of the entrance of a woman's postpartum uterus (e.g., the balloon inflates to have a volumetric capacity up to 300 milliliters, the balloon inflates to have a volumetric capacity greater than 300 milliliters), and has a diameter between 5 and 14 cm (with a mean diameter of approximately 10 cm). The inflatable balloon in the first specific example can also withstand an internal pressure of at least 5 psi, and can be reversed to a contracted configuration 148' upon delivery of the fluid or gas from the interior of the inflatable balloon.

Figure 5B:
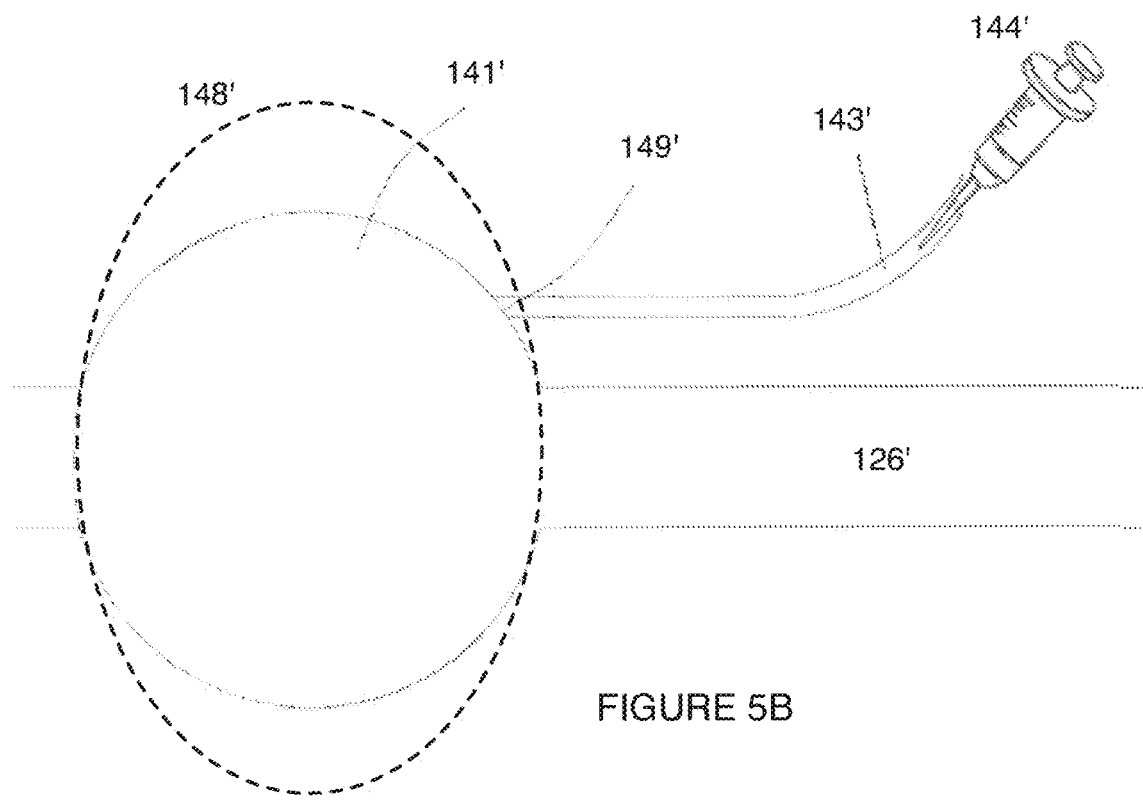

In the first specific example, as shown in FIGS. 5A and 5B, the inflatable balloon surrounds the connecting tube 126 coupled to the suction end 120, such that the connecting tube 126 is isolated from and passes entirely through the inflatable balloon. A separate delivery conduit 143, coupleable to a fluid or gas source 144, then transfers a gas or fluid through an opening into the inflatable balloon. The delivery conduit in the first specific example is composed of silicon, but may alternatively be composed of any other suitable material (e.g., rubber, plastic, silicone, silastic, plastic, polyethylene, polyurethane).

In the first specific example, the seal 141 may alternatively be expanded by producing a chemical reaction (e.g., mixture of an acid with a base, or any reaction that produces a volumetric expansion) within the interior of the sealing balloon. For instance, an acidic solution may be isolated from a chemical base within the sealing balloon, and upon mixture of the acidic solution with the chemical base, a resulting chemical reaction may produce a controlled, volumetric expansion of the sealing balloon by the production of a gas within the sealing balloon.

Figure 6:
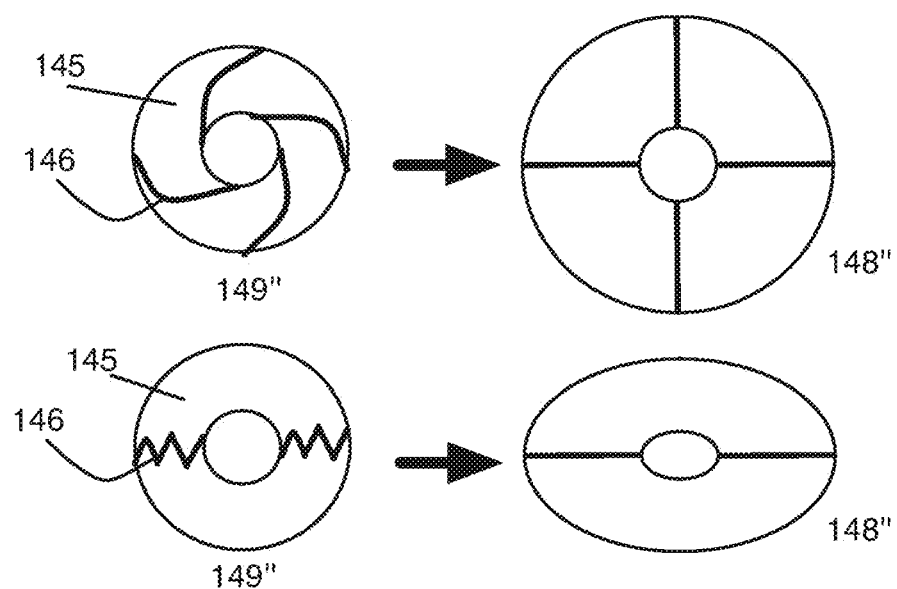
FIGS. 6 and 7 depict examples of sealing module variations.

In a second specific example of the first variation, the seal 141" comprises a membrane 145 and at least one deformable member 146, and is configured to expand radially outward into a first configuration 148" and to contract radially inward into a second configuration 149" upon manipulation of the deformable member 146. Upon delivering the suction end 120 transvaginally, the seal 141" in the second specific example is configured to be situated in the second configuration 149", within the vaginal canal. As shown in FIG. 6, the deformable member 146 may be configured to produce an expansion in one, two, or three dimensions (e.g., upon release of a compressed elastically deformable member), and to produce a contraction in one, two, or three dimensions (e.g., upon compression of an elastically deformable member). Alternatively, the deformable member 146 may be a brace attached to the membrane 145 that can outwardly push the membrane 145 into the first configuration 148" and can inwardly pull the membrane 145 into the second configuration 148". In another alternative version of the second example, the deformable member 146 may be a shape-memory material, such as nitinol, that outwardly pushes the membrane 145 into a first configuration 148" in one environment (e.g., within the body), and inwardly pulls the membrane 145 into a second configuration 148" in another environment (e.g., outside of the body).

Figure 7:
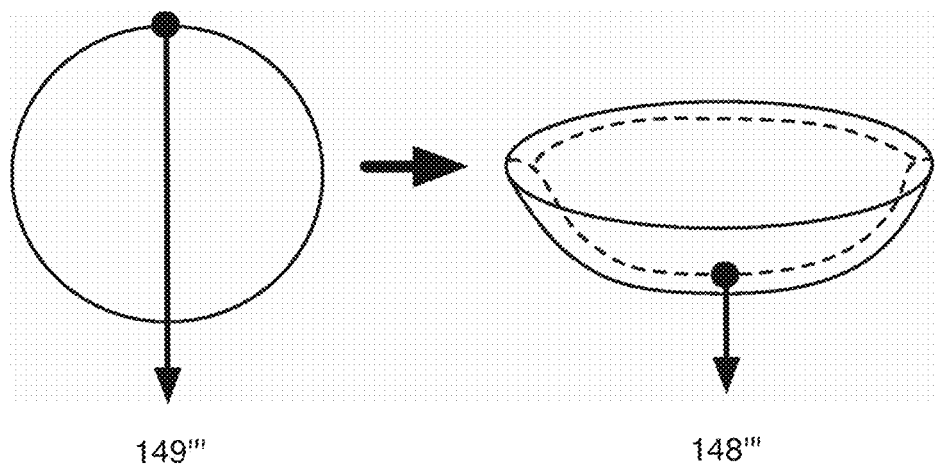

In a third specific example of the first variation, the seal 141''' is configured to take on a first geometric configuration 148''' upon an axial deformation of the seal 141" and to take on a second geometric configuration 149''' in response to a reverse deformation of the seal 141". Upon delivering the suction end 120 transvaginally, the seal 141''' in the third specific example is configured to be situated, in the first geometric configuration 149", within the vaginal canal. In the third specific example, the seal 141''' may be structurally configured with a wall that produces a sealing configuration 148''' upon axial deformation and to produce a non-sealing configuration 149''' upon removal of the axial deformation, as shown in FIG. 7. The wall may further comprise ridges or other structures that control deformation into the sealing configuration 148". Alternatively, the seal 141" may be composed of an incompressible, deformable material, such that axial deformation produces an outward expansion to form the seal, and removal of the axial deformation results in an inward contraction that reverses the seal. In another alternative version of the third example, the seal 141''' may comprise a shape-memory material, such as nitinol, that forms a sealing configuration 148''' in one environment (e.g., within the body), and forms a non-sealing configuration 149''' in another environment (e.g., outside of the body).

In a fourth specific example of the first variation, the seal 141'''' comprises a porous material (e.g., sponge, polymer hydrogel) that is configured to deform into an expanded configuration 148'''' upon absorption of a fluid, and to be in a non-expanded configuration 149'''' in the absence of a fluid. The porous material may be inserted into the body in a non-expanded configuration 1497 and may form the expanded configuration 148'''' of the seal upon absorption of blood, uterine fluids, or any other fluids. The seal 141'''' of the fourth example may thus further function to control blood loss/hemorrhaging by absorbing blood.

In a second variation, the sealing module 140 is configured to provide a seal at the vulva in an extracorporeal manner. In an example of the second variation, the sealing module 140 comprises a membrane 146 configured to seal the entrance to the vagina external to the body. The membrane 146 has an area larger than the entrance to the vagina, such that an adequate seal may be formed. The sealing module 140 may further comprise a sealant 147 (e.g., gel or lubricant) placed between the membrane 146 and the body, such that a hermetic and airtight seal is formed at the vulva. In this manner, the entrance to the vagina is substantially sealed to allow a negative pressure to be provided within the uterus.

In other variations, the sealing module 140 may only have a single configuration 148 configured to produce a seal upon insertion into the body. Prior to insertion, the vagina or vaginal canal may be manually expanded (e.g., with a speculum operated by a health care provider), the sealing module 140 may be inserted (with the suction end 120 already inserted), and the vagina or vaginal canal may then be released to form a seal about the sealing module 140. In an example, the sealing module 140 is a substantially rigid structure that has a cross section larger than the cross section of the vaginal canal, such that the vaginal canal seals around the rigid structure.

Figure 8A:
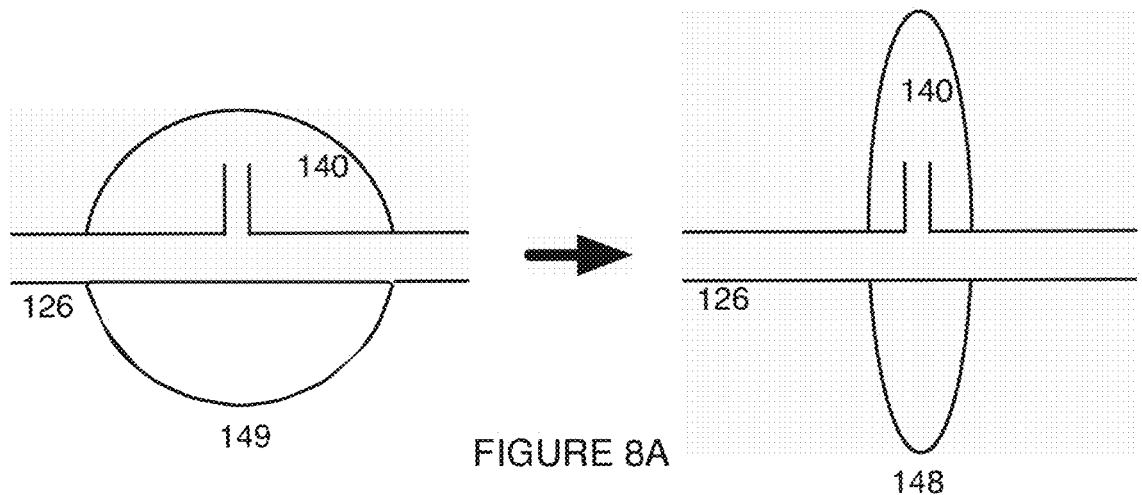
FIGS. 8A and 8B depict examples of system elements with dual functionality.
Figure 8B:
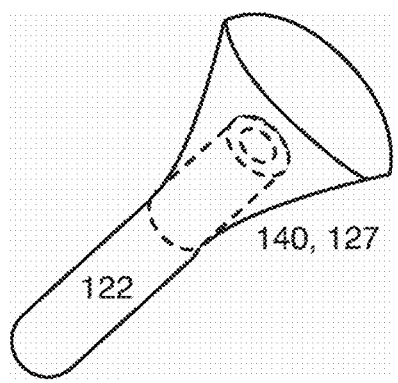

Additional variations of the sealing module 140 may comprise any suitable combination of the above variations, or combination of any of the above variations with any other suitable sealing element. Furthermore, in other variations, as shown in FIG. 8A, the connecting tube 126 of the suction module 110 may be coupled to the sealing module 140, such that a negative pressure provided by the suction module 110 contracts the uterus and produces a sealing configuration by the sealing module 140. Additionally, other variations may comprise a sealing module 140 that functions as a shield 127 (or is physically coextensive with a shield), an example of which is shown in FIG. 8B. Again, the sealing module may comprise any suitable combination or configuration of elements as described.

1.3 System—Other Elements

As shown in FIG. 1, the system 100 may further comprise a pump 130, which functions to generate the negative pressure in order to contract the uterus. The pump may comprise a clinical (e.g., hospital) suction line, vacuum device, or any appropriate pump (e.g., syringe pump, peristaltic pump) that can produce an adequate negative pressure to contract the uterus. In a specific example, the pump generates a negative pressure within the uterus of up to 3 psi. In one variation, the connecting tube 126 of the suction module 110 is configured to couple to the pump 130 in a reversible manner. However, the connecting tube 126 may also terminate in a pump element in a non-reversible manner, such that the pump 130 is integrated with the system 100. In an example, the pump element is a hollow chamber with a naturally expanded configuration. The pump element in the example may be constrained in a depressed state prior to delivering the suction end 120 into the uterus, after which the pump element is released to expand freely. Expansion of the pump element thus generates the negative pressure required to facilitate contraction of the atonic uterus.

Also shown in FIG. 1, the system 100 may further comprise a filter 150, which functions to filter fluids and other substances that have entered the connecting tube 126. The filter is preferably distal to the pump 130 and proximal to the suction end 120, such that any substance that enters the suction end 120 is filtered prior to reaching the pump 130. Alternatively or additionally, the opening(s) of the suction end 120 may comprise filters that function to pre-filter substances that enter the suction end 120. The filter 150 preferably comprises a membrane with pores that prevent passage of unwanted substances into the pump.

As a person skilled in the art will recognize from the previous detailed description and from the figures and claims, modifications and changes can be made to the preferred embodiments of the system without departing from the scope of this invention.

2. Method

Figure 9:
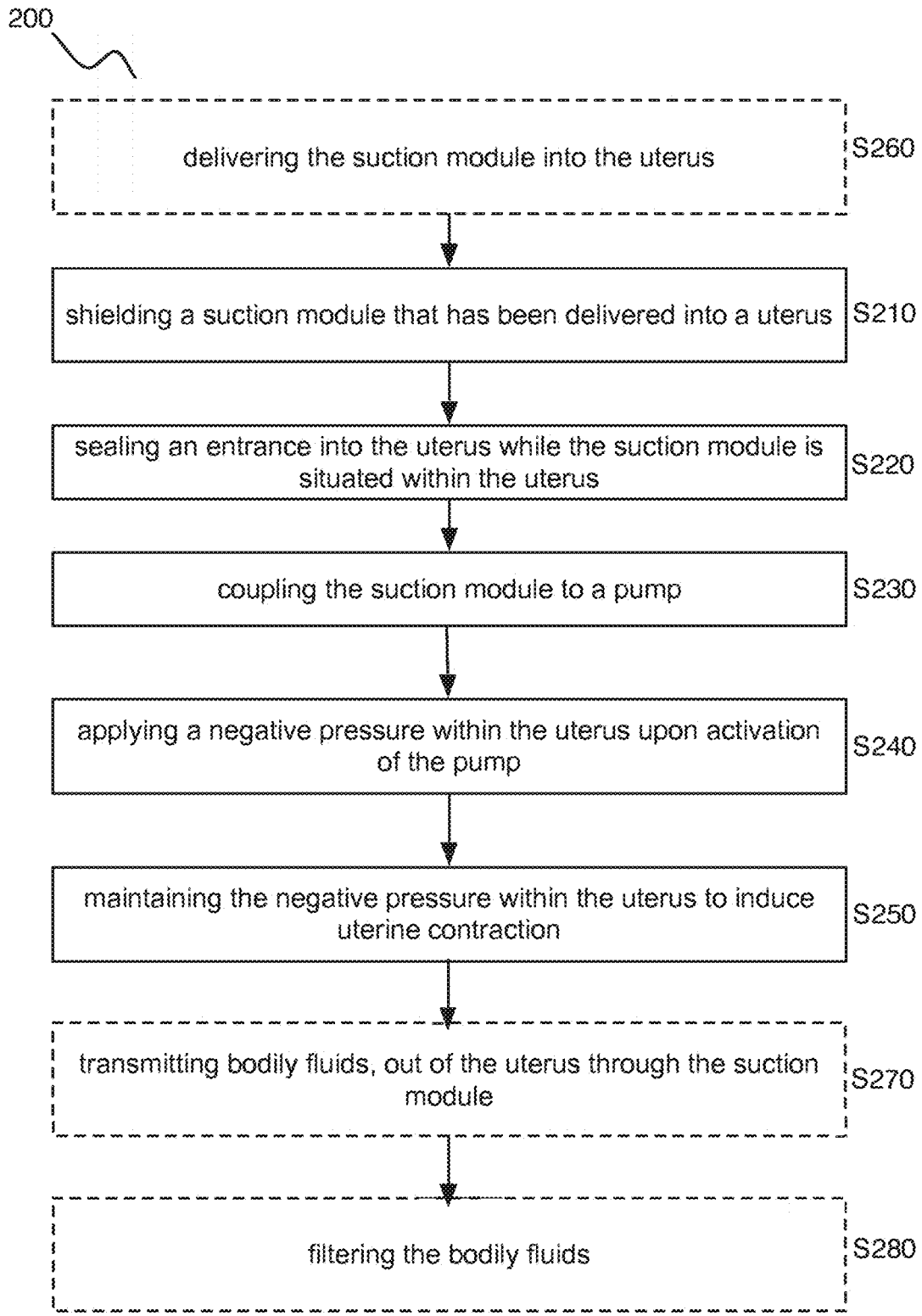
FIG. 9 depicts an embodiment of steps of a uterine hemorrhage controlling method.

As shown in FIG. 9, a uterine hemorrhage controlling method 200 comprises: shielding a suction module that has been delivered into a uterus S210, sealing an entrance into the uterus while the suction module is situated within the uterus S220; coupling the suction module to a pump S230; applying a negative pressure within the uterus upon activation of the pump S240; and maintaining the negative pressure within the uterus to induce uterine contraction S250. The method 200 may further comprise delivering the suction module into the uterus S260; transmitting bodily fluids out of the uterus through the suction module S270, and filtering the bodily fluids S280. The method 200 thus functions to reduce or entirely stop uterine hemorrhaging, in order to substantially reduce total blood lost from the uterus after childbirth. The method 200 may further function to reduce other issues associated with childbirth, including a need for a blood transfusion or a hysterectomy. Furthermore, because the method 200 is performed transvaginally, a patient may remain conscious while the method 200 is performed. The method 200 is preferably performed by the system 100 described above or using the system 1oo described above; however, the method 200 may be performed by or using any other suitable system.

Step S210 recites shielding a suction module that has been delivered into a uterus, and functions to prevent obstruction of a suction module opening, such that a negative pressure may be applied to the interior of the uterus. Preferably, Step S210 is performed using any suitable variation of the shield and/or dual-functioning suction end described above. For example, Step S210 may be implemented using a shield to shield the suction tube, or may be implemented using a suction tube with medially oriented openings, such that the suction tube dually functions as a shield. However, Step S210 may be formed using any suitable element or method to prevent uterine tissue or any other tissue from blocking an opening of the suction module.

Step S220 recites sealing an entrance into the uterus while the suction module is situated within the uterus, and functions to enable maintenance of a negative pressure within the uterus. Preferably, Step S220 is performed using any suitable variation of the sealing module described above, an example of which is shown in FIG. 10; however, Step S220 may be formed using any suitable element or method configured to seal an entrance into the uterus. In a first example, Step S220 comprises expanding an inflatable balloon seal (e.g., by delivering fluid or gas into the balloon) at the entrance to the uterus. In the first example, the inflatable balloon may be inflated near the distal end of the vagina to a pressure of up to 5 psi. In a second example, S220 comprises producing a radial expansion of a membrane seal. In a third example, S220 comprises axially deforming a seal to transform the seal into a sealing configuration. In a fourth example, S220 comprises applying a sealant external to the vaginal canal and placing a sealing membrane at the entrance to the vaginal canal to create a seal. In a fifth example, S220 comprises manually expanding the vaginal canal, placing a sealing element into the vaginal canal, and then allowing the vaginal canal to contract about the sealing element to create the seal. Other variations of S220 may comprise other manipulations of system variations described above, or any other suitable method of sealing an entrance to the uterus.

Figure 12:
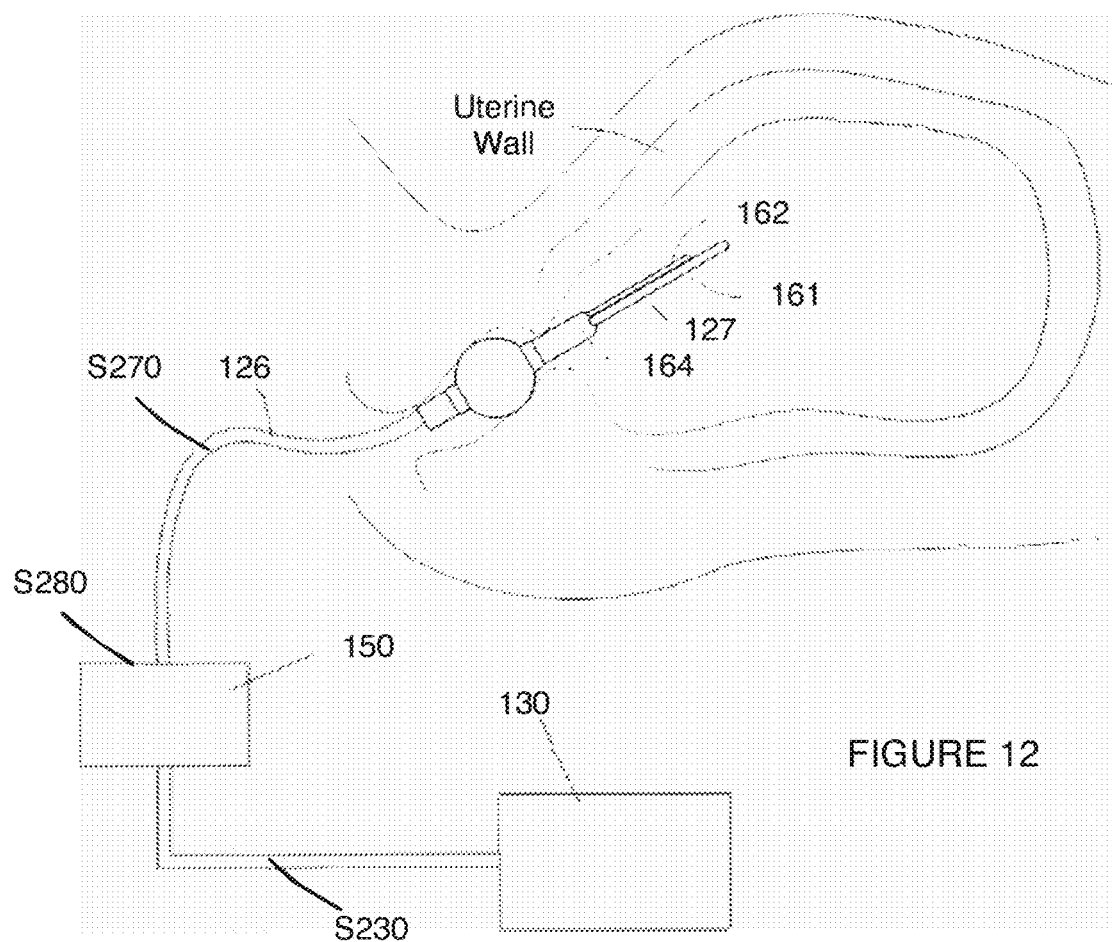
FIG. 12 is a schematic showing an implementation of an embodiment of a uterine hemorrhage controlling method.

Step S230 recites coupling the suction module to a pump, and functions to prepare the suction module to transmit a negative pressure to the interior of the uterus. Step S230 may be performed before or after the suction module has been delivered to the interior of the uterus. In one variation, Step S230 may comprise coupling a connecting tube of the suction module to a clinical suction line, as shown in FIG. 12, but in other variations, Step S230 may alternatively comprise coupling any suitable portion of a suction module to any suitable pump element.

Step S240 recites applying a negative pressure within the uterus upon activation of the pump, and functions to generate a stimulus that enables an atonic uterus to contract, thus counteracting uterine atony. The negative pressure may result in a uniform mechanical stimulus or a non-uniform mechanical stimulus that results in contraction of the uterus to control hemorrhaging. For instance, the negative pressure may be a hydrostatic pressure. In an example, the pump is activated to produce a flow rate of less than 30 liters per minute, and a negative pressure of up to 3 psi within the uterus, while monitoring pressure levels using a pressure sensor.

Step S250 recites maintaining the negative pressure within the uterus to induce uterine contraction, and functions to facilitate closing of exposed uterine arterioles in the uterine wall. Step S250 may further function to decrease the possibility of the uterus returning to an atonic state. Preferably, the negative pressure is maintained until hemorrhaging has been reduced to safe levels or has substantially stopped. The negative pressure may also be maintained as long as deemed necessary to maintain the uterine contraction, and in a specific example, is maintained for between 1 and 24 hours. In an example, maintenance of a negative pressure of 3 psi within the uterus causes the uterus to fully contract within 15 seconds. Additionally, Step S250 may comprise monitoring a patient's blood pressure and heart rate while the negative pressure is maintained, and eliminating the negative pressure after levels have returned to a normal level. In an example, the negative pressure may be eliminated once the patient's systolic blood pressure is between 90 and 140 mm Hg, and the patient's heart rate is between 40 and 100 beats per minute. The negative pressure is preferably eliminated once hemorrhaging has been reduced to safe levels or has substantially stopped. The negative pressure may be eliminated by removal of a seal to the entrance to the uterus, which may be performed in any suitable manner (e.g., deflation of an inflatable balloon seal, radial contraction of a membrane, etc.).

Figure 11:
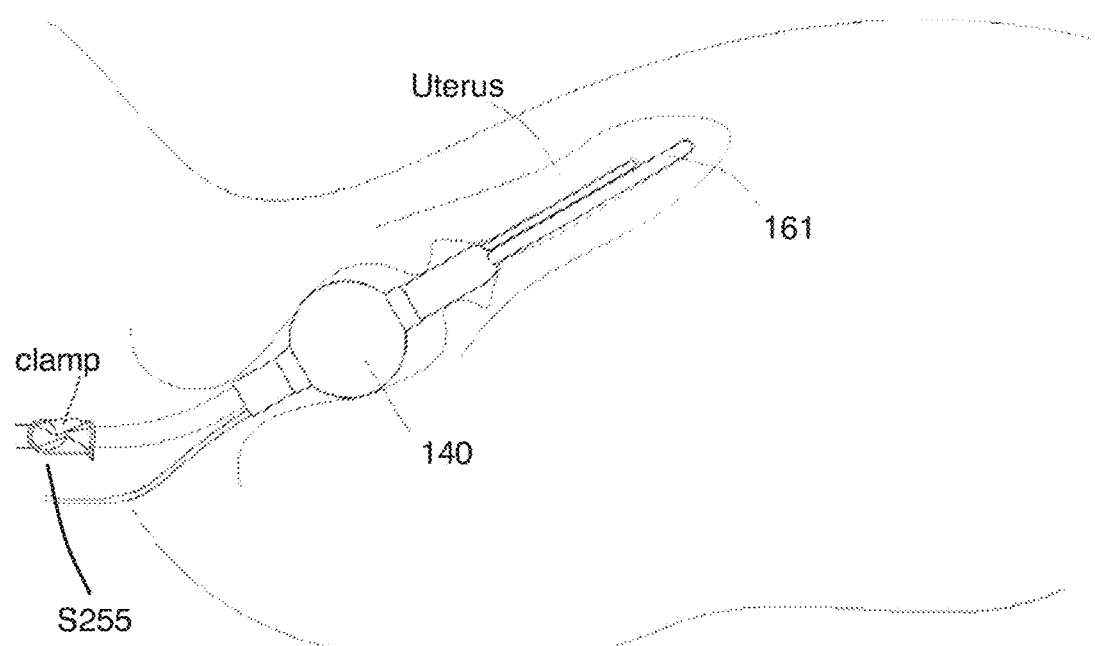

As shown in FIG. 11, Step S250 may further comprise Step S255, which recites obstructing a connection between the suction module and the pump. Step S255 functions to maintain a negative pressure within the uterus, even upon deactivation of the pump. Step S255 also functions to prevent premature elimination of a negative pressure within the uterus (e.g., upon deactivation of the pump). Step S255 may further function to allow intrauterine tissue to re-energize, and may further function to facilitate removal of the suction module from the uterus. In one variation, Step S255 may comprise clamping a connecting tube between the suction module and the pump, as shown in FIG. 11. In another variation, the connection may be a valved connection, such that Step S255 comprises shutting a valve to obstruct a connection between the suction module and the pump. Step S255 may, however, comprise any suitable variation of obstructing a connection between the suction module and the pump.

Figure 10:
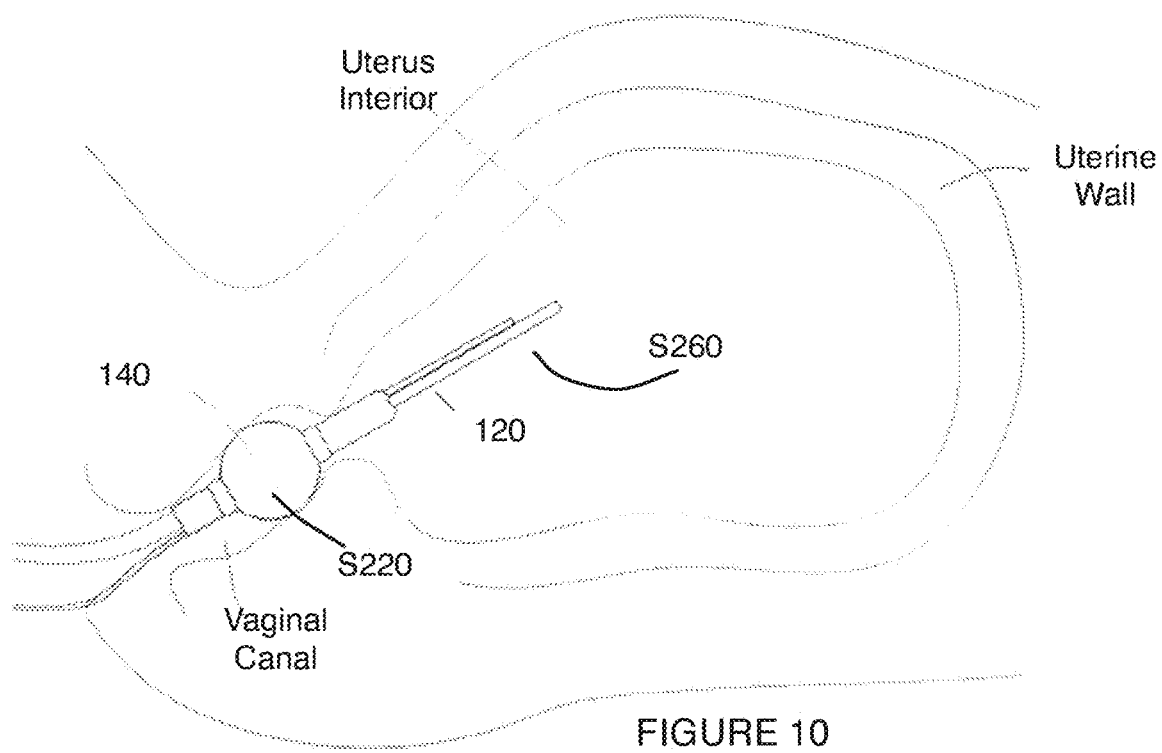
FIGS. 10-11 depict embodiments of steps of a uterine hemorrhage controlling method.

As shown in FIGS. 9 and 10, the method 200 may further comprise Step S260, which recites delivering the suction module into the uterus. Step S260 functions to initiate treatment of an atonic uterus. Preferably, Step S260 comprises delivering the suction end of the suction module described above into the uterus; however, Step S260 may comprise delivering any suitable suction module into the uterus. The reverse of Step S260, as shown in FIG. 11, may comprise removing the suction module from the uterus, and in an example, may comprise clamping a connecting tube to the suction module, deactivating the pump, and then withdrawing the suction module from the uterus. Other variations of Step S260 and the reverse of Step S260 may comprise any other suitable methods of delivering the suction module into the uterus and removing the suction module from the uterus.

As shown in FIGS. 9 and 12, the method 200 may further comprise Step S270, which recites transmitting bodily fluids out of the uterus through the suction module. Step S270 functions to remove fluids from within the uterus in the process of inducing contraction of an atonic uterus. The bodily fluids preferably pass into at least one opening of the suction module and into the connecting tube of the suction module; however, Step S270 may alternatively comprise any other means for transmitting bodily fluids out of the uterus.

Also shown in FIGS. 9 and 12, the method 200 may further comprise Step S270, which recites filtering the bodily fluids. Step S280 functions to prevent unwanted substances from entering the pump, which allows the pump to maintain proper function and to continually apply a negative pressure. Step S280 may further function to enable monitoring of blood loss. For example, filtering the bodily fluids S280 into a transparent container may allow a caretaker to monitor a quantity of blood lost during implementation of the method 100. Step S280 may occur at any point along the suction module, distal to the pump; however, Step S280 preferably occurs along a connecting tube coupled to the pump.

The FIGURES illustrate the architecture, functionality and operation of possible implementations of systems and methods according to preferred embodiments, example configurations, and variations thereof. In this regard, each block in the flowchart or block diagrams may represent a module, segment, or step, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved.

The system and method of the embodiments can be embodied and/or implemented at least in part as a machine configured to receive a computer-readable medium storing computer-readable instructions. The instructions can be executed by computer-executable components integrated with an application, applet, host, server, network, website, communication service, communication interface, hardware/firmware/software elements of a user computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the preferred embodiments of the invention without departing from the scope of this invention defined in the following claims.

We claim:

1. An anti-hemorrhaging device, comprising:
   a tubular distal section configured to be placed within a uterus, the tubular distal section comprising a distal inner channel and an outer tubular wall;
   at least one hole extending from the distal inner channel through the outer tubular wall so as to create at least one opening along an outer surface of the tubular distal section;
   a proximal section having a proximal inner channel fluidically connected to the distal inner channel, the proximal section configured to attach to a vacuum source, wherein activation of the vacuum source is configured to pull vacuum through the proximal and distal inner channels and the at least one hole so as to collapse the uterus; and
   a shield coupled to and extending at least partially axially along the tubular distal section, the shield diverging outward from the tubular distal section and spaced radially away from the at least one opening, the shield configured to prevent tissue from occluding the at least one hole when vacuum is applied.

2. The device of claim 1, wherein the shield is flexible.

3. The device of claim 1, wherein the shield is rigid.

4. The device of claim 1, wherein the shield at least partially encapsulates the at least one hole.

5. The device of claim 1, wherein the tubular distal section forms a loop.

6. The device of claim 5, wherein the at least one hole is on an interior portion of the loop.

7. The device of claim 1, wherein the tubular distal section is flexible, the flexible tubular distal section configured to reversibly deform for delivery to the uterus.

8. The device of claim 1, further comprising a pump configured to act as the vacuum source.

9. The device of claim 1, further comprising a collection container fluidically coupled to the tubular distal section and configured to collect fluid removed from the uterus when vacuum is applied.

10. The device of claim 1, further comprising a seal positioned between the tubular distal section and the proximal section, the seal configured to expand from a collapsed configuration to an expanded configuration to seal the anti-hemorrhaging device within the uterus.

11. The device of claim 1, wherein the at least one hole comprises a plurality of holes.

12. An anti-hemorrhaging device, comprising:
a tubular distal section configured to be placed within a uterus, the tubular distal section comprising a distal inner channel and an outer tubular wall;
at least one hole extending from the distal inner channel through the outer tubular wall so as to create at least one opening along an outer surface of the tubular distal section;
a proximal section having a proximal inner channel fluidically connected to the distal inner channel, the proximal section configured to attach to a vacuum source, wherein activation of the vacuum source is configured to pull vacuum through the proximal and distal inner channels and the at least one hole so as to collapse the uterus; and
a shield coupled to the tubular distal section on a first side of the at least one opening and extending beyond the at least one opening to a second side of the at least one opening, the shield configured to prevent tissue from occluding the at least one hole when vacuum is applied.

13. The device of claim 12, wherein the shield is flexible.

14. The device of claim 12, wherein the shield is rigid.

15. The device of claim 12, wherein the shield at least partially encapsulates the at least one hole.

16. The device of claim 12, wherein the tubular distal section forms a loop.

17. The device of claim 16, wherein the at least one hole is on an interior portion surface of the loop.

18. The device of claim 12, wherein the tubular distal section is flexible, the flexible tubular distal section configured to reversibly deform for delivery to the uterus.

19. The device of claim 12, further comprising a pump configured to act as the vacuum source.

20. The device of claim 12, further comprising a collection container fluidically coupled to the tubular distal section and configured to collect fluid removed from the uterus when vacuum is applied.

21. The device of claim 12, further comprising a seal positioned between the tubular distal section and the proximal section, the seal configured to expand from a collapsed configuration to an expanded configuration to seal the anti-hemorrhaging device within the uterus.

22. The device of claim 12, wherein the at least one hole comprises a plurality of holes.

* * * * *